(12) United States Patent
Palomer et al.

(10) Patent No.: US 8,507,684 B2
(45) Date of Patent: Aug. 13, 2013

(54) 1-CYCLOPROPYL-8-METHYL-7-[5-METHYL-6-(METHYLAMINO)-3-PYRIDINYL]-4-OXO-1,4-DIHYDRO-3-QUINOLINECARBOXYLIC ACID SALTS

(75) Inventors: Albert Palomer, Barcelona (ES); Luis Anglada, Barcelona (ES)

(73) Assignee: Ferrer Internacional S.A., Barcelona (ES)

( * ) Notice: Subject to any disclaimer, the term of this patent is extended or adjusted under 35 U.S.C. 154(b) by 0 days.

(21) Appl. No.: 13/639,405

(22) PCT Filed: Apr. 6, 2010

(86) PCT No.: PCT/EP2010/054506
§ 371 (c)(1),
(2), (4) Date: Oct. 24, 2012

(87) PCT Pub. No.: WO2011/124249
PCT Pub. Date: Oct. 13, 2011

(65) Prior Publication Data
US 2013/0040989 A1    Feb. 14, 2013

(51) Int. Cl.
*C07D 215/02*    (2006.01)
*A61K 31/4412*    (2006.01)

(52) U.S. Cl.
USPC .......................................... 546/156; 514/312

(58) Field of Classification Search
None
See application file for complete search history.

(56) References Cited

U.S. PATENT DOCUMENTS

| | | | |
|---|---|---|---|
| 6,335,447 | B1 | 1/2002 | Hayashi et al. |
| 2010/0099704 | A1 | 4/2010 | Hirota |

FOREIGN PATENT DOCUMENTS

| | | |
|---|---|---|
| EP | 1 731 138 A1 | 12/2006 |
| EP | 1 941 880 A1 | 7/2008 |
| JP | 2002-356426 A | 12/2002 |
| JP | 2003-226643 A | 8/2003 |
| JP | 2007-119456 A | 5/2007 |
| WO | 2007/015453 A1 | 2/2007 |

OTHER PUBLICATIONS

Tetsumi Yamakawa et al.; "Liquid formulation of a novel non-fluorinated topical quinolone, T-3912, utilizing the synergic solubilizing . . . " Journal of Controlled Release; No. 86; pp. 101-113; 2003.

*Primary Examiner* — Brandon Fetterolf
*Assistant Examiner* — Rayna B Rodriguez
(74) *Attorney, Agent, or Firm* — Birch, Stewart, Kolasch & Birch, LLP.

(57) ABSTRACT

There is provided a salt of 1-cyclopropyl-8-methyl-7-[5-methyl-6-(methylamino)-3-pyridinyl]-4-oxo-1,4-dihydro-3-quinolinecarboxylic acid selected from the group consisting of citrate, hemi-fumarate, maleate, L-tartrate, mesylate, hydrochloride, potassium, and sodium salts.

5 Claims, 16 Drawing Sheets

1-CYCLOPROPYL-8-METHYL-7-[5-METHYL-6-(METHYLAMINO)-3-PYRIDINYL]-4-OXO-1,4-DIHYDRO-3-QUINOLINECARBOXYLIC ACID SALTS

TECHNICAL FIELD

The present invention relates to citrate, hemi-fumarate, maleate, L-tartrate, mesylate, hydrochloride, potassium, and sodium salts of 1-cyclopropyl-8-methyl-7-[5-methyl-6-(methylamino)-3-pyridinyl]-4-oxo-1,4-dihydro-3-quinolinecarboxylic acid. These salts are characterized by an improved solubility in water.

BACKGROUND ART

1-Cyclopropyl-8-methyl-7-[5-methyl-6-(methylamino)-3-pyridinyl]-4-oxo-1,4-dihydro-3-quinolinecarboxylic acid is disclosed in U.S. Pat. No. 6,335,447. This substance is known under its International Nonproprietary Name of ozenoxacin. Its chemical formula is:

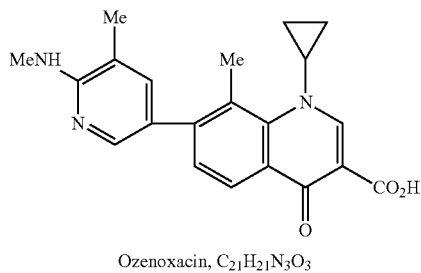

Ozenoxacin, $C_{21}H_{21}N_3O_3$

Ozenoxacin is a known antibacterial agent. Some dermal compositions comprising ozenoxacin have been disclosed in JP2002356426A, JP2003226643A, EP1731138A1, and WO2007015453A1. Ophthalmic compositions of ozenoxacin have been disclosed in JP2007119456A, and Yamakawa, T. et al., *Journal of Controlled Release* (2003), 86(1), 101-103.

The above referenced U.S. Pat. No. 6,335,447 generically refers to salts but does not disclose any specific salt of the des-fluoroquinolone compounds (I).

Figure 1:
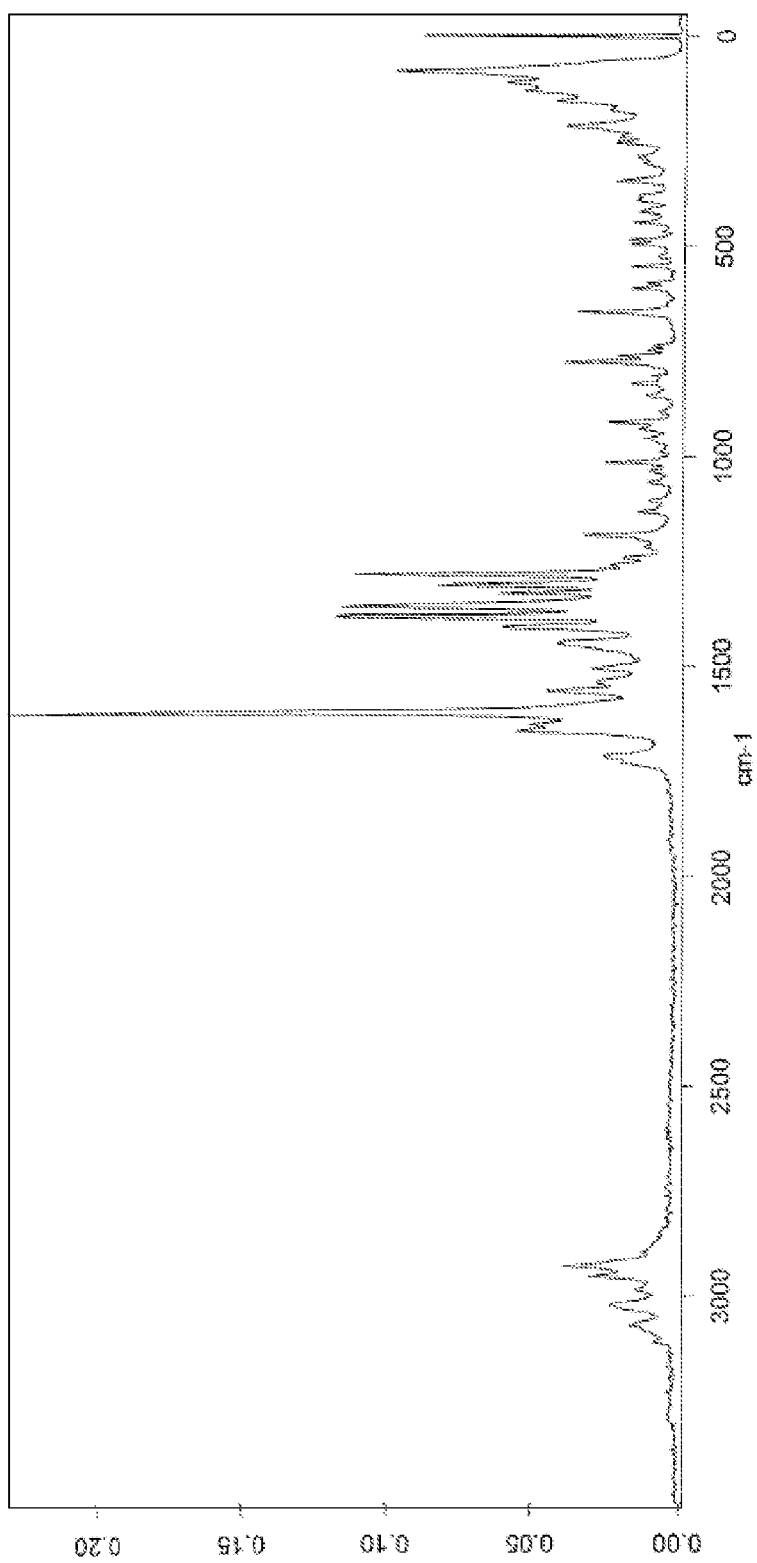
FIG. 1 shows a FT-Raman spectrum of the compound of Example 1.

In the FT-Raman spectra the axis of the ordinates shows intensity and the axis of the abscissas shows the Raman shift ($cm^{-1}$).

In the IR spectrum the axis of the ordinates shows percentage of absorption and the axis of the abscissas shows the wavelength ($cm^{-1}$).

In the powder X-ray diffraction patterns the axis of the ordinates shows the diffraction intensity and the axis of the abscissas shows the diffraction angle (2θ).

SUMMARY OF THE INVENTION

Ozenoxacin shows a low solubility in water. It is well known that pharmaceuticals with very poor water solubility present formulation problems due to their slow rate of dissolution. Moreover, the efficacy of drugs with low water solubility is severely limited when systemic administration is required, and large inter-individual variations of absorption can occur, with drugs of low solubility frequently not being absorbed properly.

Accordingly, in order to supply better pharmaceutical compounds of this drug substance, it has been desired that soluble salts of ozenoxacin be discovered.

The present inventors have investigated a variety of salts of ozenoxacin and have found that particular salts of ozenoxacin have higher solubility than the base drug.

In a first aspect, the present invention refers to pharmaceutical salts of 1-cyclopropyl-8-methyl-7-[5-methyl-6-(methylamino)-3-pyridinyl]-4-oxo-1,4-dihydro-3-quinolinecarboxylic acid, characterized in that their solubility is ≧0.050 mg/mL of water.

In a second aspect, the present invention refers to pharmaceutical salts of 1-cyclopropyl-8-methyl-7-[5-methyl-6-(methyl amino)-3-pyridinyl]-4-oxo-1,4-dihydro-3-quinolinecarboxylic acid selected from the group consisting of citrate, hemi-fumarate, maleate, L-tartrate, mesylate, hydrochloride, potassium, and sodium salts.

In a third aspect, the present invention refers to pharmaceutical compositions comprising a pharmaceutical salt of 1-cyclopropyl-8-methyl-7-[5-methyl-6-(methylamino)-3-pyridinyl]-4-oxo-1,4-dihydro-3-quinolinecarboxylic acid selected from the group consisting of citrate, hemi-fumarate, maleate, L-tartrate, mesylate, hydrochloride, potassium, and sodium salts as an active ingredient.

In a fourth aspect, the present invention refers to pharmaceutical salts of 1-cyclopropyl-8-methyl-7-[5-methyl-6-(methylamino)-3-pyridinyl]-4-oxo-1,4-dihydro-3-quinolinecarboxylic acid selected from the group consisting of citrate, hemi-fumarate, maleate, L-tartrate, mesylate, hydrochloride, potassium, and sodium salts for use as a medicament.

In a fifth aspect, the present invention refers to the use of pharmaceutical salts of 1-cyclopropyl-8-methyl-7-[5-methyl-6-(methylamino)-3-pyridinyl]-4-oxo-1,4-dihydro-3- quinolinecarboxylic acid selected from the group consisting of citrate, hemi-fumarate, maleate, L-tartrate, mesylate, hydrochloride, potassium, and sodium salts for the manufacture of a medicament for the treatment or prevention of bacterial infections.

In a sixth aspect, the present invention refers to pharmaceutical salts of 1-cyclopropyl-8-methyl-7-[5-methyl-6-(methylamino)-3-pyridinyl]-4-oxo-1,4-dihydro-3-quinolinecarboxylic acid selected from the group consisting of citrate, hemi-fumarate, maleate, L-tartrate, mesylate, hydrochloride, potassium, and sodium salts for use in the treatment or prevention of bacterial infections.

Another object of this invention is to provide novel methods to treat a subject suffering or being at risk of a bacterial infection by administering a therapeutically effective amount of a pharmaceutical salt of 1-cyclopropyl-8-methyl-7-[5-methyl-6-(methylamino)-3-pyridinyl]-4-oxo-1,4-dihydro-3-quinolinecarboxylic acid selected from the group consisting of citrate, hemi-fumarate, maleate, L-tartrate, mesylate, hydrochloride, potassium, and sodium salts.

DETAILED DESCRIPTION OF THE INVENTION

In a preferred embodiment, the present invention refers to pharmaceutical salts according to the first aspect of the invention, characterized in that their solubility is $\geq 0.075$ mg/mL of water.

Preferably, the present invention refers to pharmaceutical salts according to the second aspect of the invention which are:
a) 1-cyclopropyl-8-methyl-7-[5-methyl-6-(methylamino)-3-pyridinyl]-4-oxo-1,4-dihydro-3-quinolinecarboxylic acid citrate;
b) 1-cyclopropyl-8-methyl-7-[5-methyl-6-(methylamino)-3-pyridinyl]-4-oxo-1,4-dihydro-3-quinolinecarboxylic acid hemi-fumarate;
c) 1-cyclopropyl-8-methyl-7-[5-methyl-6-(methylamino)-3-pyridinyl]-4-oxo-1,4-dihydro-3-quinolinecarboxylic acid maleate;
d) 1-cyclopropyl-8-methyl-7-[5-methyl-6-(methylamino)-3-pyridinyl]-4-oxo-1,4-dihydro-3-quinolinecarboxylic acid L-tartrate;
e) 1-cyclopropyl-8-methyl-7-[5-methyl-6-(methylamino)-3-pyridinyl]-4-oxo-1,4-dihydro-3-quinolinecarboxylic acid mesylate;
f) 1-cyclopropyl-8-methyl-7-[5-methyl-6-(methylamino)-3-pyridinyl]-4-oxo-1,4-dihydro-3-quinolinecarboxylic acid hydrochloride;
g) 1-cyclopropyl-8-methyl-7-[5-methyl-6-(methylamino)-3-pyridinyl]-4-oxo-1,4-dihydro-3-quinolinecarboxylic acid hydrochloride hydrate;
h) 1-cyclopropyl-8-methyl-7-[5-methyl-6-(methylamino)-3-pyridinyl]-4-oxo-1,4-dihydro-3-quinolinecarboxylic acid hydrochloride monohydrate;
i) 1-cyclopropyl-8-methyl-7-[5-methyl-6-(methylamino)-3-pyridinyl]-4-oxo-1,4-dihydro-3-quinolinecarboxylic acid potassium salt; and
j) 1-cyclopropyl-8-methyl-7-[5-methyl-6-(methylamino)-3-pyridinyl]-4-oxo-1,4-dihydro-3-quinolinecarboxylic acid sodium salt.

According to an embodiment, the citrate salt has characteristic peaks in the Raman spectrum at ($cm^{-1}$): 2930, 1640, 1390, 1370, 1290, 1210, 780 and 670. In particular, the citrate salt is characterized by the Raman spectrum as shown in FIG. 1.

Figure 2:
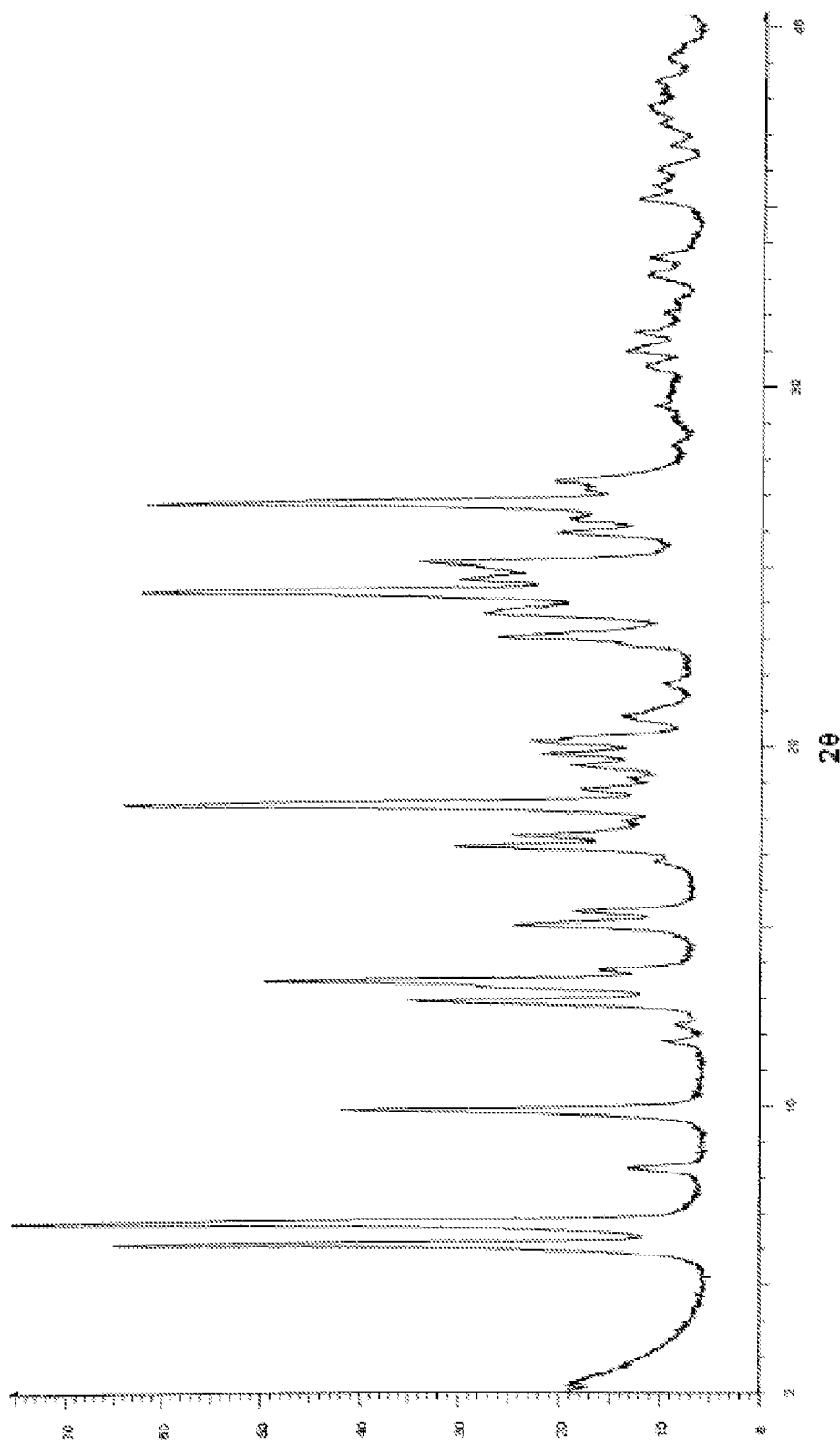
FIG. 2 shows a powder X-ray diffraction pattern of the compound of Example 1.

According to an embodiment, the citrate salt has characteristic peaks in the powder X-ray diffraction pattern at ($2\theta$): 5.9, 6.7, 9.8, 12.3, 18.2, 24.1, and 26.5; or at 5.9, 6.7, 8.3, 9.8, 11.8, 12.3, 14.0, 15.3, 17.1, 17.4, 18.2, 18.8, 19.4, 19.7, 20.2, 23.0, 23.6, 24.1, 24.5, 25.1, 25.9, 26.5 and 27.3. In particular, the citrate salt is characterized by the powder X-ray diffraction pattern as shown in FIG. 2.

Figure 3:
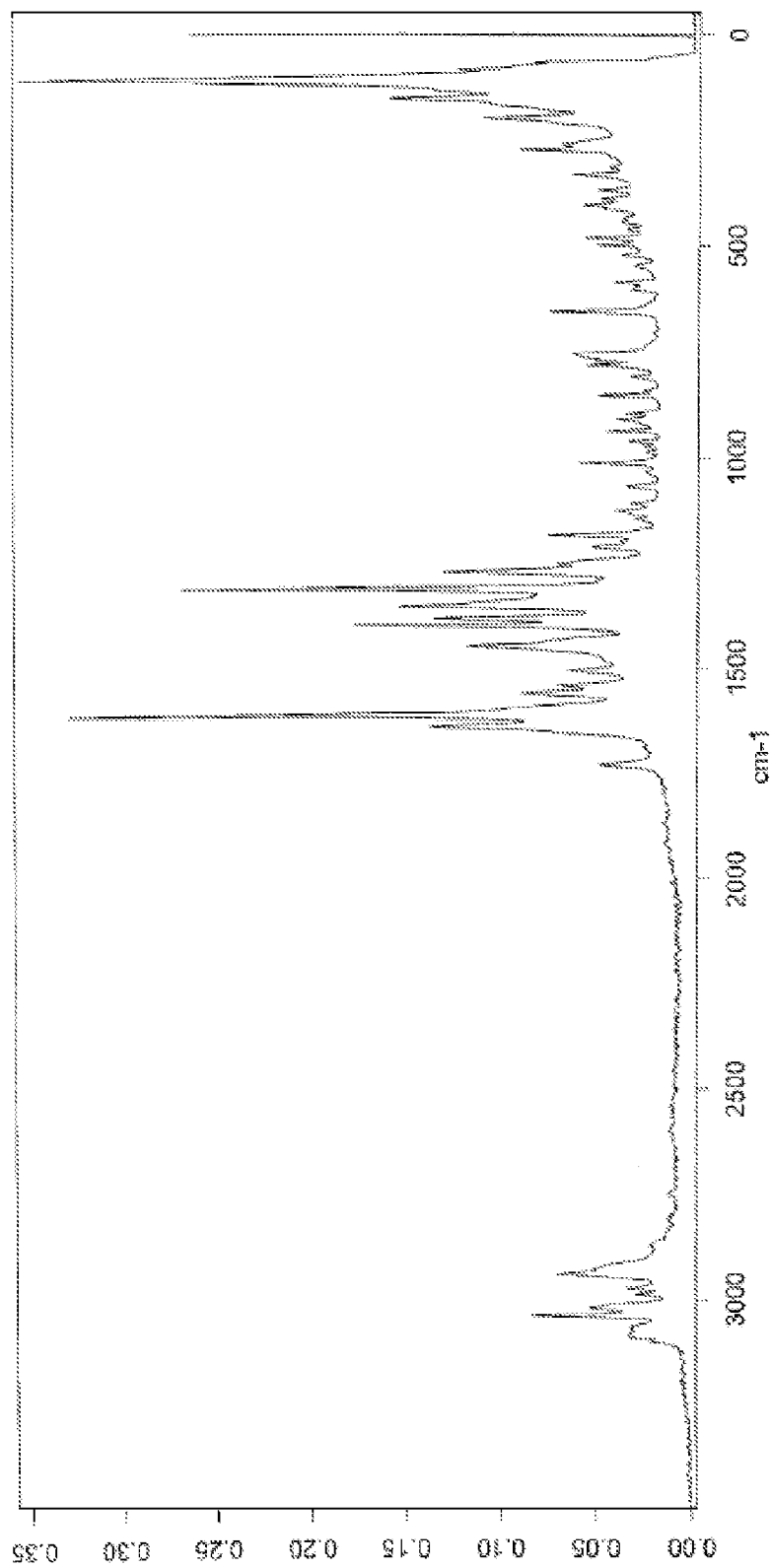
FIG. 3 shows a FT-Raman spectrum of the compound of Example 2.

According to an embodiment, the hemi-fumarate salt has characteristic peaks in the Raman spectrum at ($cm^{-1}$): 3042, 2942, 1635, 1400, and 1317. In particular, the hemi-fumarate salt is characterized by the Raman spectrum as shown in FIG. 3.

Figure 4:
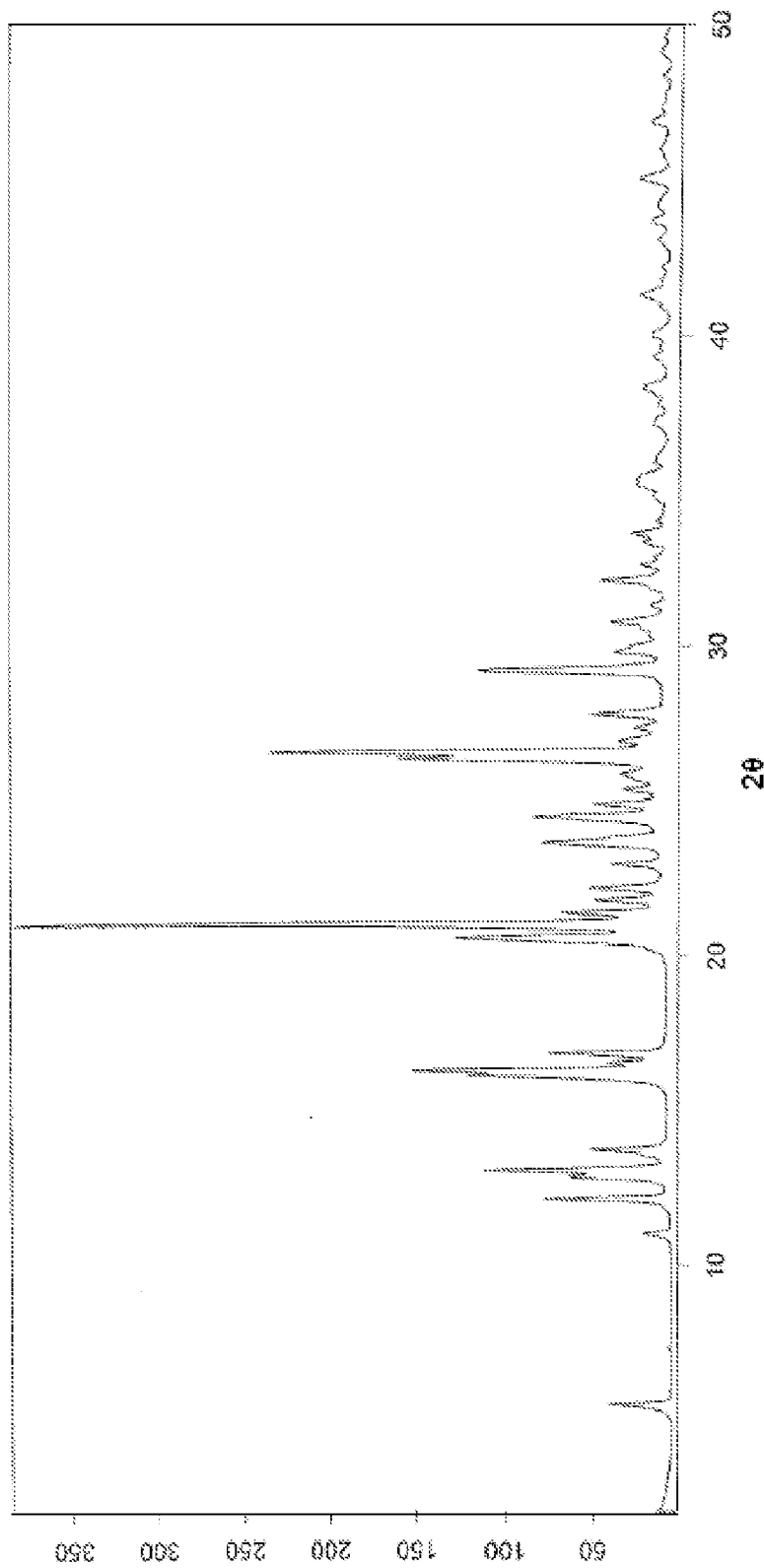
FIG. 4 shows a powder X-ray diffraction pattern of the compound of Example 2.

According to an embodiment, the hemi-fumarate salt has characteristic peaks in the powder X-ray diffraction pattern at ($2\theta$): 5.5, 12.0, 12.8, 16.2, 20.9, 26.5 and 29.1; or at 5.5, 12.0, 12.8, 13.0, 16.2, 16.8, 20.6, 20.9, 23.6, 24.4, 26.5, 27.8, and 29.1. In particular, the hemi-fumarate salt is characterized by the powder X-ray diffraction pattern as shown in FIG. 4.

Figure 5:
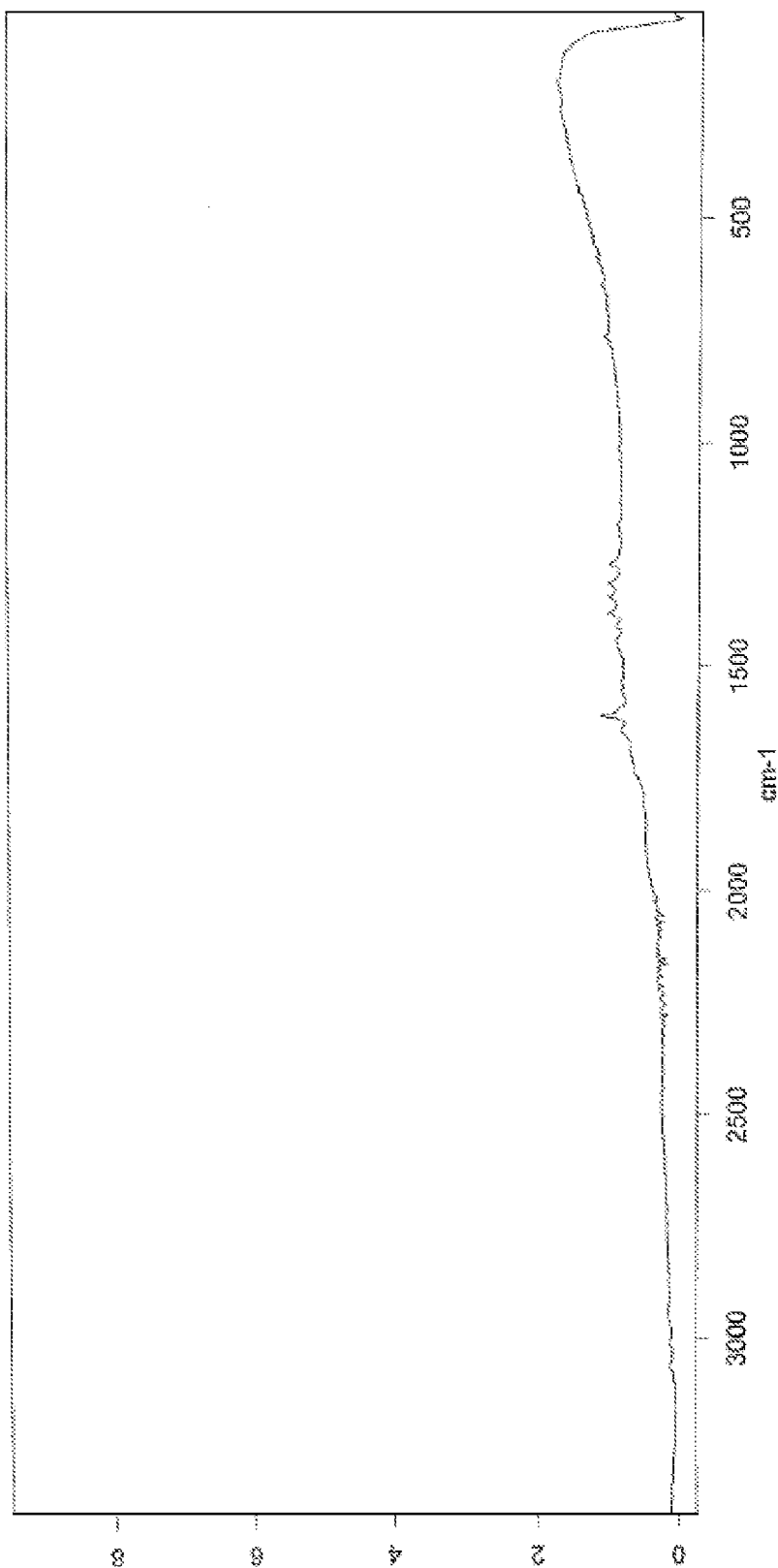
FIG. 5 shows a FT-Raman spectrum of the compound of Example 3.

According to an embodiment, the maleate salt has characteristic peaks in the Raman spectrum at ($cm^{-1}$): 617. In particular, the maleate salt is characterized by the Raman spectrum as shown in FIG. 5.

Figure 6:
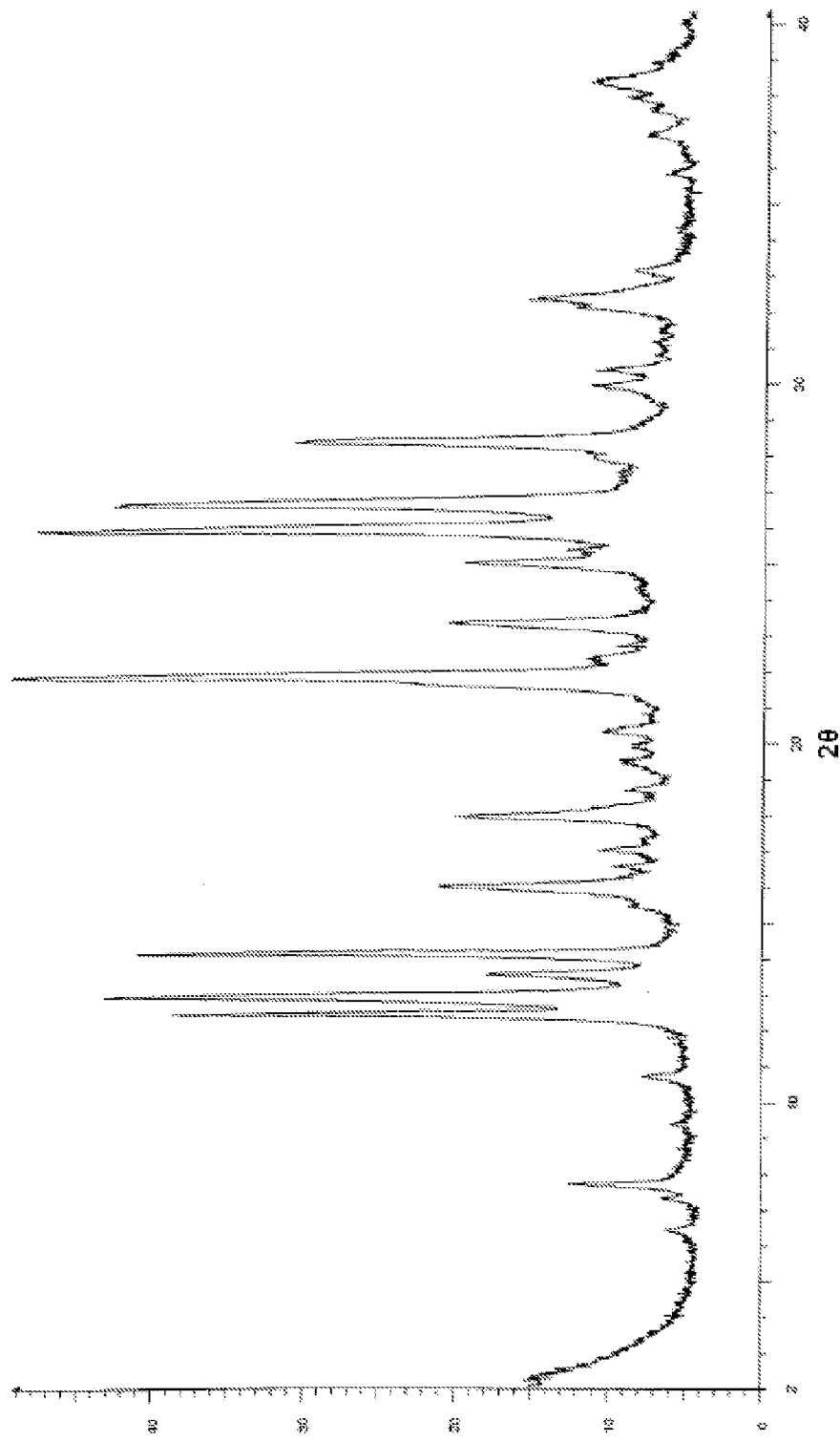
FIG. 6 shows a powder X-ray diffraction pattern of the compound of Example 3.

According to an embodiment, the maleate salt has characteristic peaks in the powder X-ray diffraction pattern at ($2\theta$): 7.7, 12.3, 12.8, 14.0, 21.5, 25.7, 26.3 and 28.2; or at 7.7, 12.3, 12.8, 13.6, 14.0, 16.0, 17.9, 21.5, 23.2, 24.95, 25.7, 26.3, 28.2, 29.8, 30.3, 32.3 and 38.3. In particular, the maleate salt is characterized by the powder X-ray diffraction pattern as shown in FIG. 6.

Figure 7:
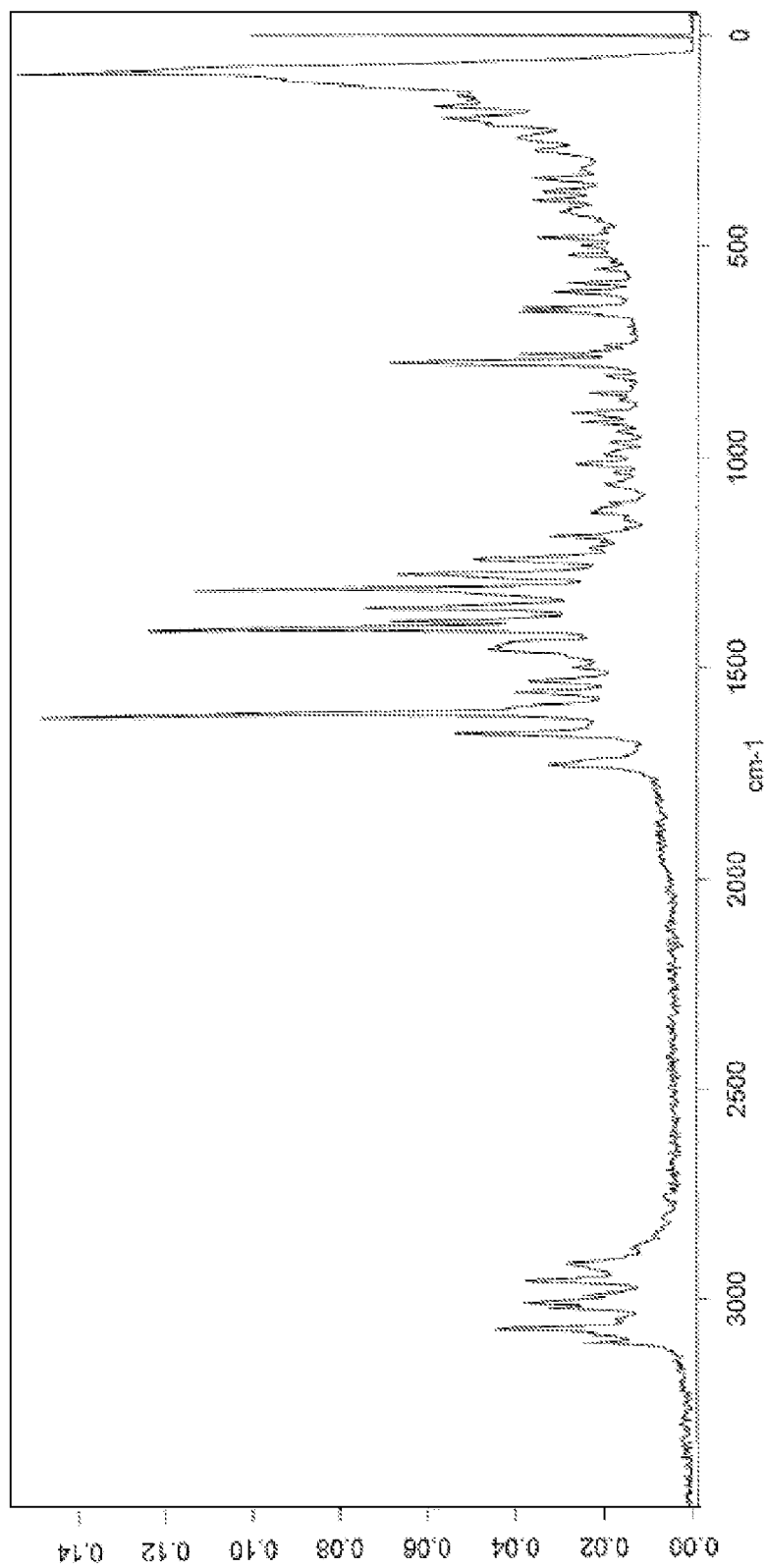
FIG. 7 shows a FT-Raman spectrum of the compound of Example 4.

According to an embodiment, the L-tartrate salt has characteristic peaks in the Raman spectrum at ($cm^{-1}$): 3067, 3005, 2960, 1625, 1417, 1367, 1325, 1285, 1247 and 783. In particular, the L-tartrate salt is characterized by the Raman spectrum as shown in FIG. 7.

Figure 8:
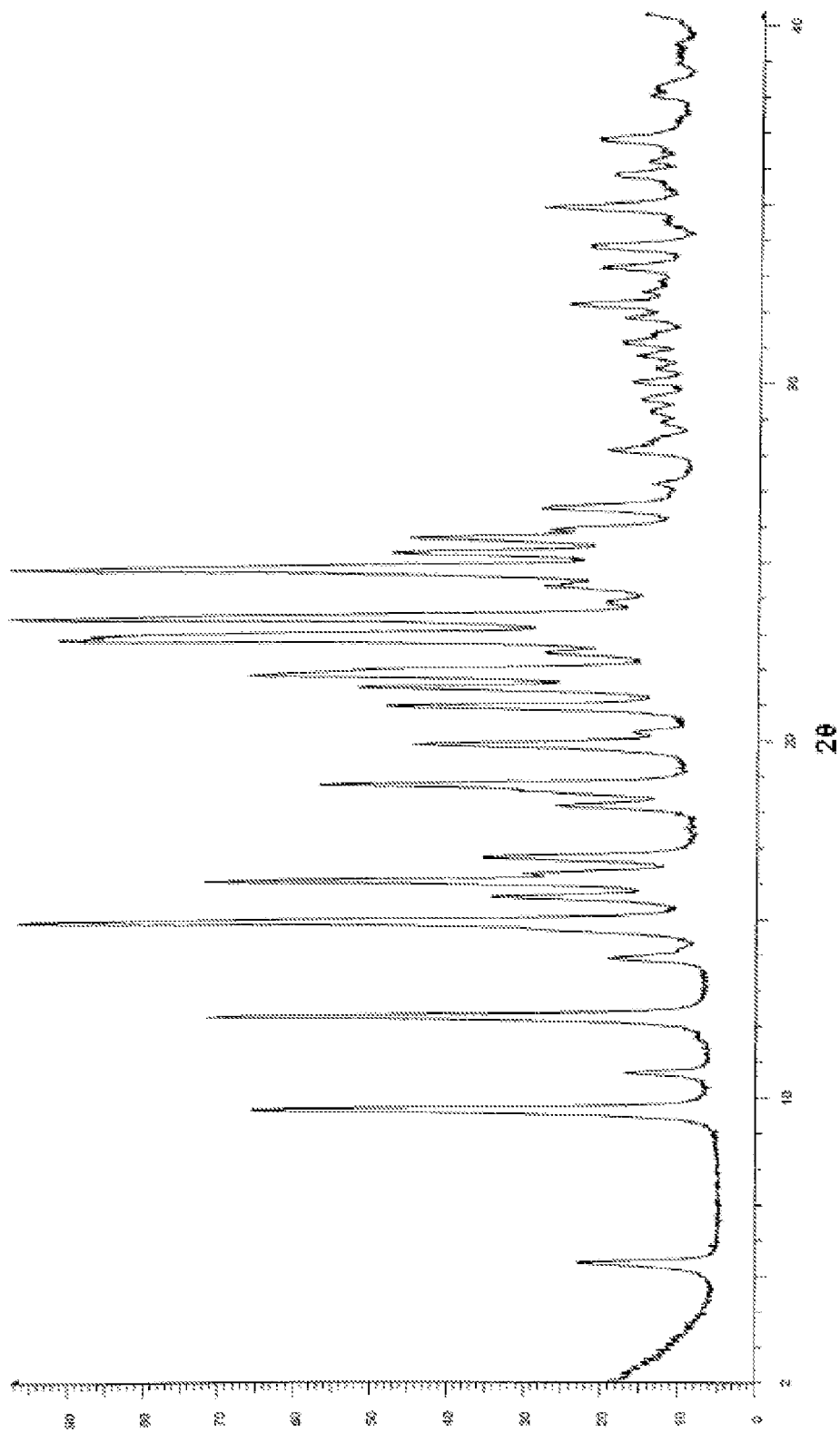
FIG. 8 shows a powder X-ray diffraction pattern of the compound of Example 4.

According to an embodiment, the L-tartrate salt has characteristic peaks in the powder X-ray diffraction pattern at ($2\theta$): 5.3, 9.4, 12.1, 14.7, 16.0, 18.7, 22.6, 23.1 and 24.5; or at 5.3, 9.4, 10.7, 12.1, 13.9, 14.7, 15.6, 16.0, 16.7, 18.1, 18.7, 19.8, 20.9, 21.3, 21.7, 22.6, 23.1, 24.5, 25.2, 25.7, 26.4 and 34.9. In particular, the L-tartrate salt is characterized by the powder X-ray diffraction pattern as shown in FIG. 8.

Figure 9:
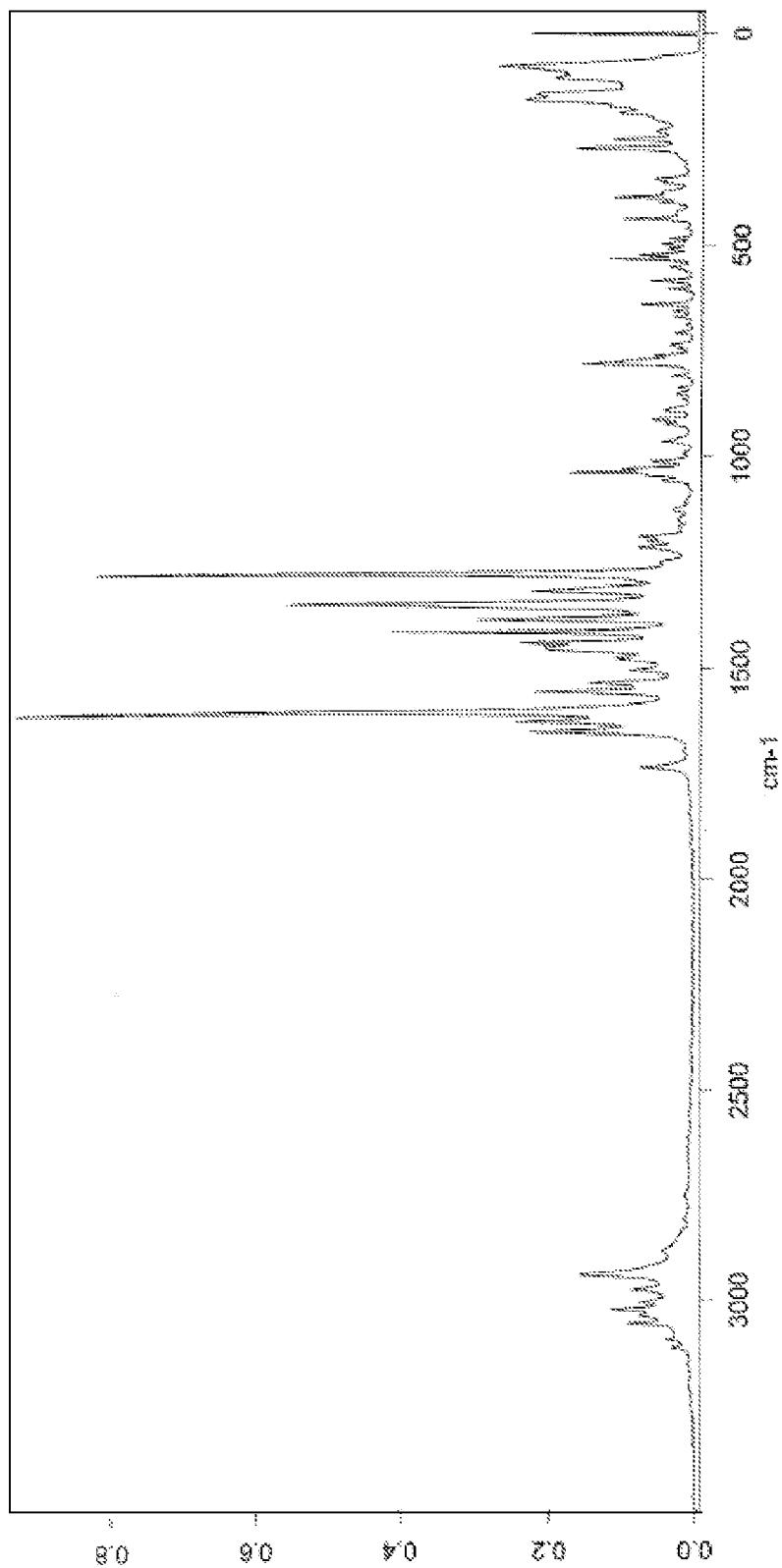
FIG. 9 shows a FT-Raman spectrum of the compound of Example 5.

According to an embodiment, the mesylate salt has characteristic peaks in the Raman spectrum at ($cm^{-1}$): 2942, 1608, 1365 and 1300. In particular, the mesylate salt is characterized by the Raman spectrum as shown in FIG. 9.

Figure 10:
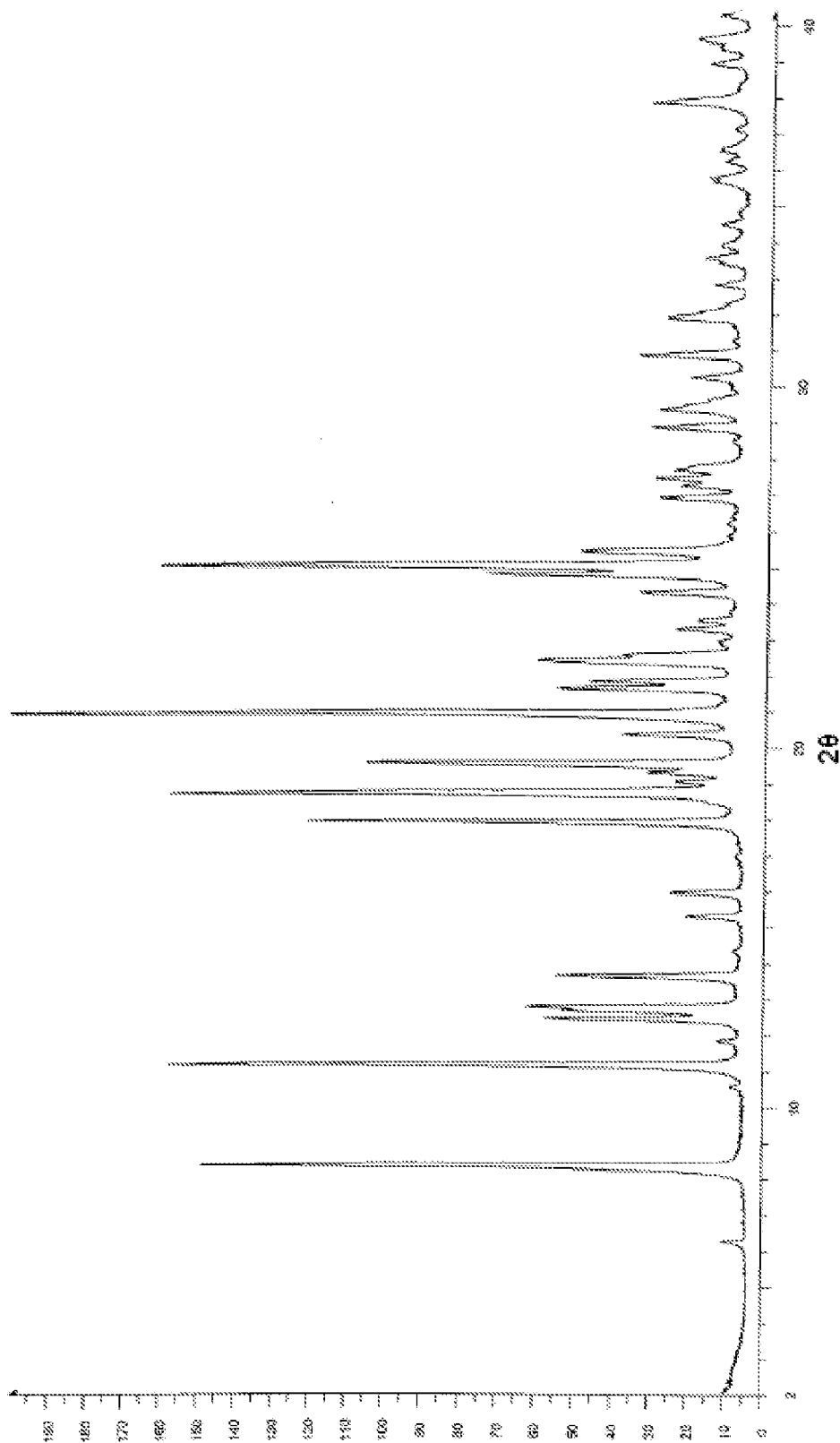
FIG. 10 shows a powder X-ray diffraction pattern of the compound of Example 5.

According to an embodiment, the mesylate salt has characteristic peaks in the powder X-ray diffraction pattern at ($2\theta$): 8.3, 11.2, 17.9, 18.6, 20.8 and 29.9; or at 8.3, 11.2, 12.4, 12.8, 13.7, 17.9, 18.6, 19.5, 20.8, 22.4 and 29.9. In particular, the mesylate salt is characterized by the powder X-ray diffraction pattern as shown in FIG. 10.

Figure 11:
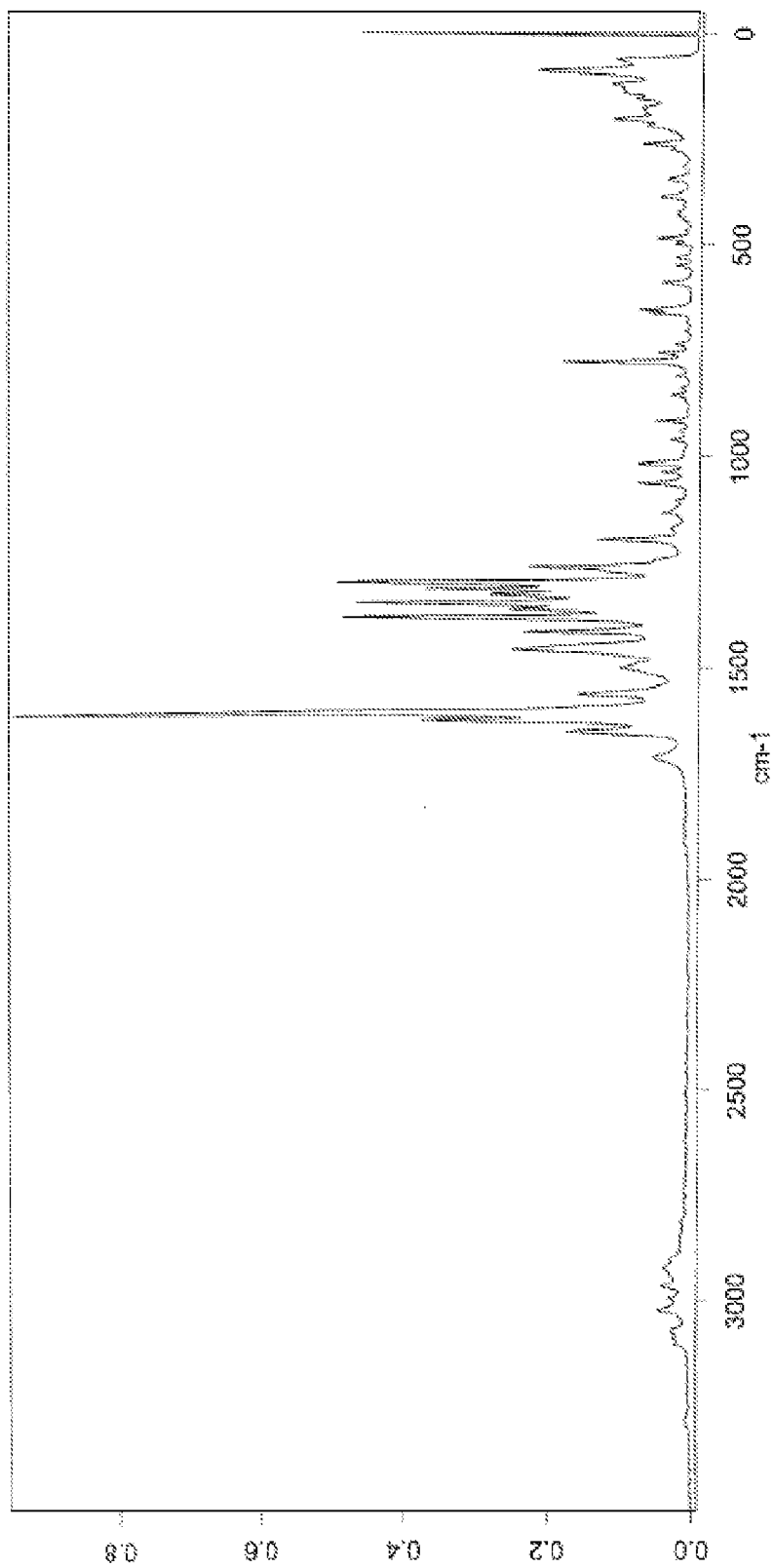
FIG. 11 shows a FT-Raman spectrum of the compound of Example 6.

According to an embodiment, the hydrochloride monohydrate salt has characteristic peaks in the Raman spectrum at ($cm^{-1}$): 1615, 1380, 1350 and 1300. In particular, the hydrochloride monohydrate salt is characterized by the Raman spectrum as shown in FIG. 11.

Figure 12:
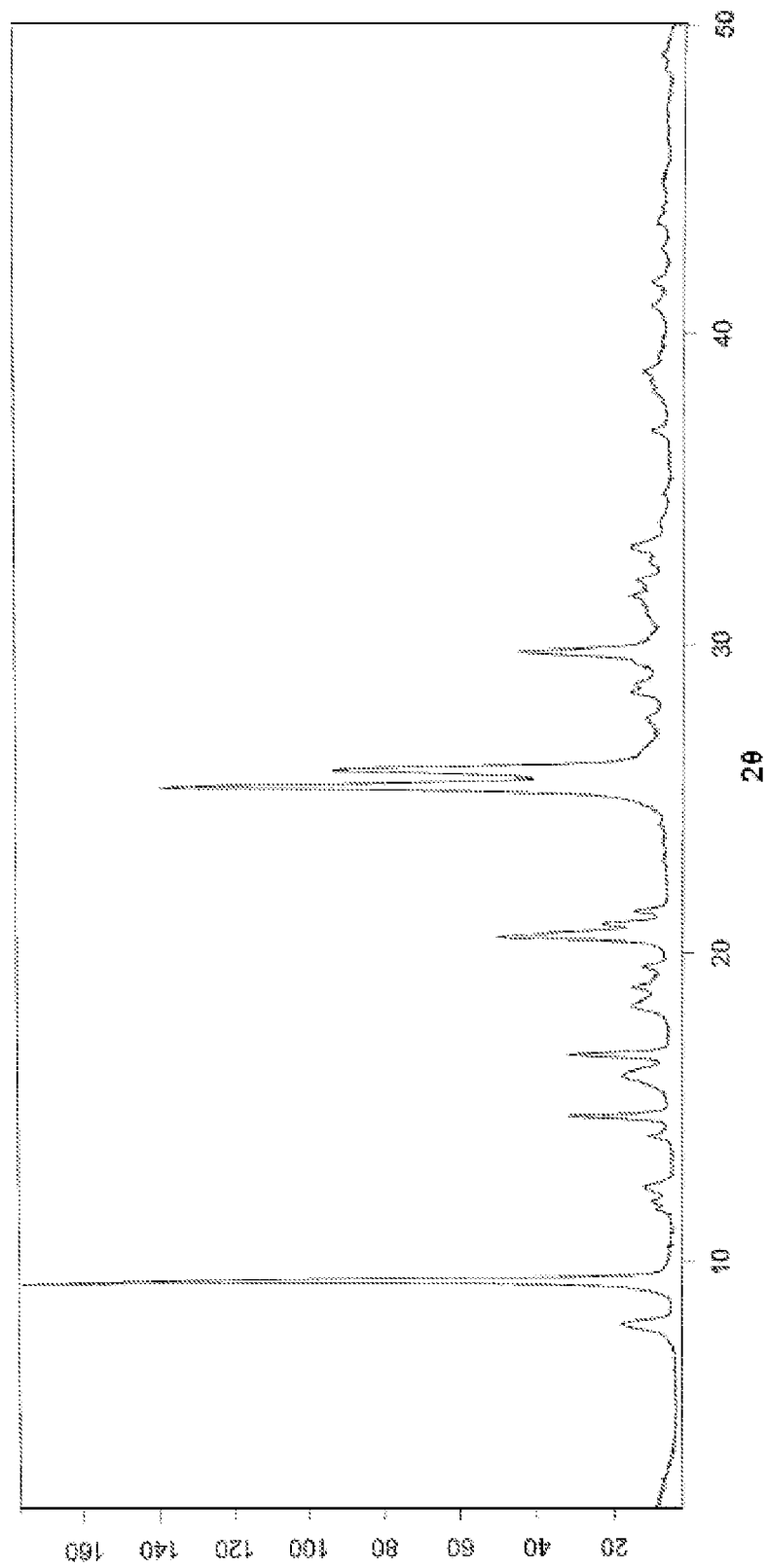
FIG. 12 shows a powder X-ray diffraction pattern of the compound of Example 6.

According to an embodiment, the hydrochloride monohydrate salt has characteristic peaks in the powder X-ray diffraction pattern at ($2\theta$): 9.5, 25.4 and 26.0; or at 8.6, 9.5, 14.7, 16.7, 20.6, 25.4, 26.0 and 29.8. In particular, the hydrochloride monohydrate salt is characterized by the powder X-ray diffraction pattern as shown in FIG. 12.

Figure 13:
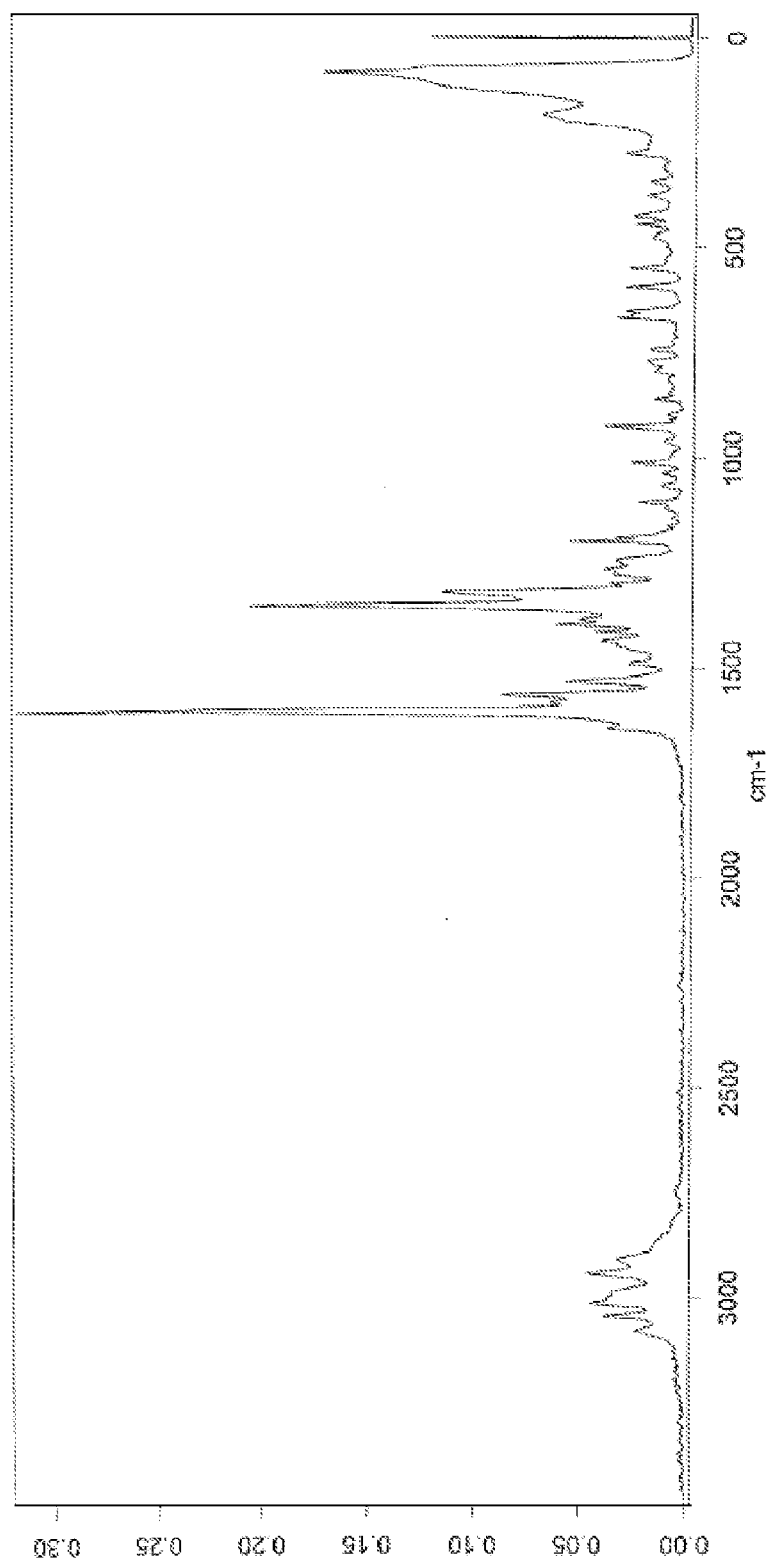
FIG. 13 shows a FT-Raman spectrum of the compound of Example 7.

According to an embodiment, the potassium salt has characteristic peaks in the Raman spectrum at ($cm^{-1}$): 3050, 3017, 2940, 1600, 1358 and 1325. In particular, the potassium salt is characterized by the Raman spectrum as shown in FIG. 13.

Figure 14:
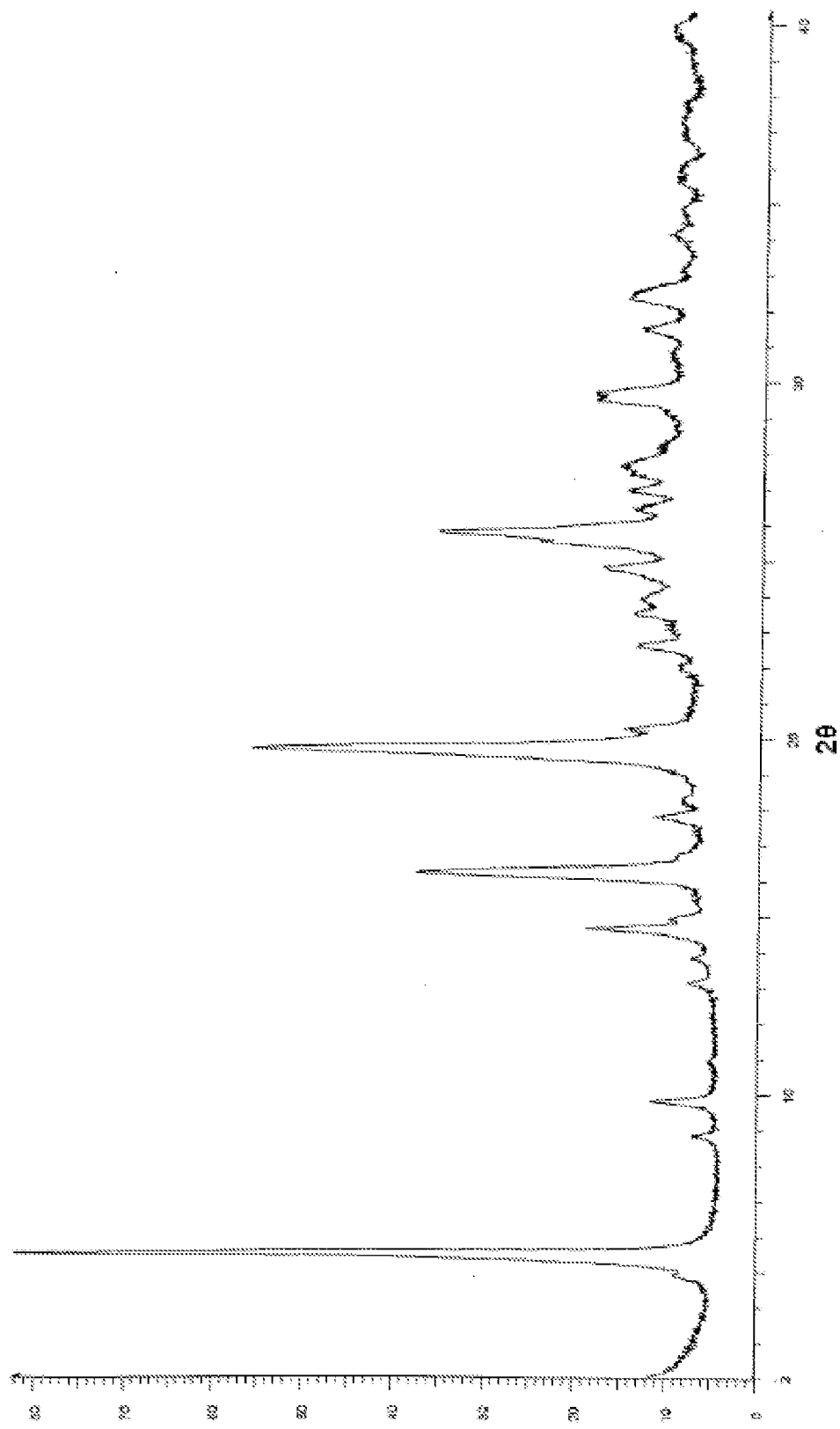
FIG. 14 shows a powder X-ray diffraction pattern of the compound of Example 7.

According to an embodiment, the potassium salt has characteristic peaks in the powder X-ray diffraction pattern at ($2\theta$): 5.8, 16.2, 19.7 and 25.7; or at 5.8, 9.9, 14.7, 16.2, 19.7 and 25.7. In particular, the potassium salt is characterized by the powder X-ray diffraction pattern as shown in FIG. 14.

Figure 15:
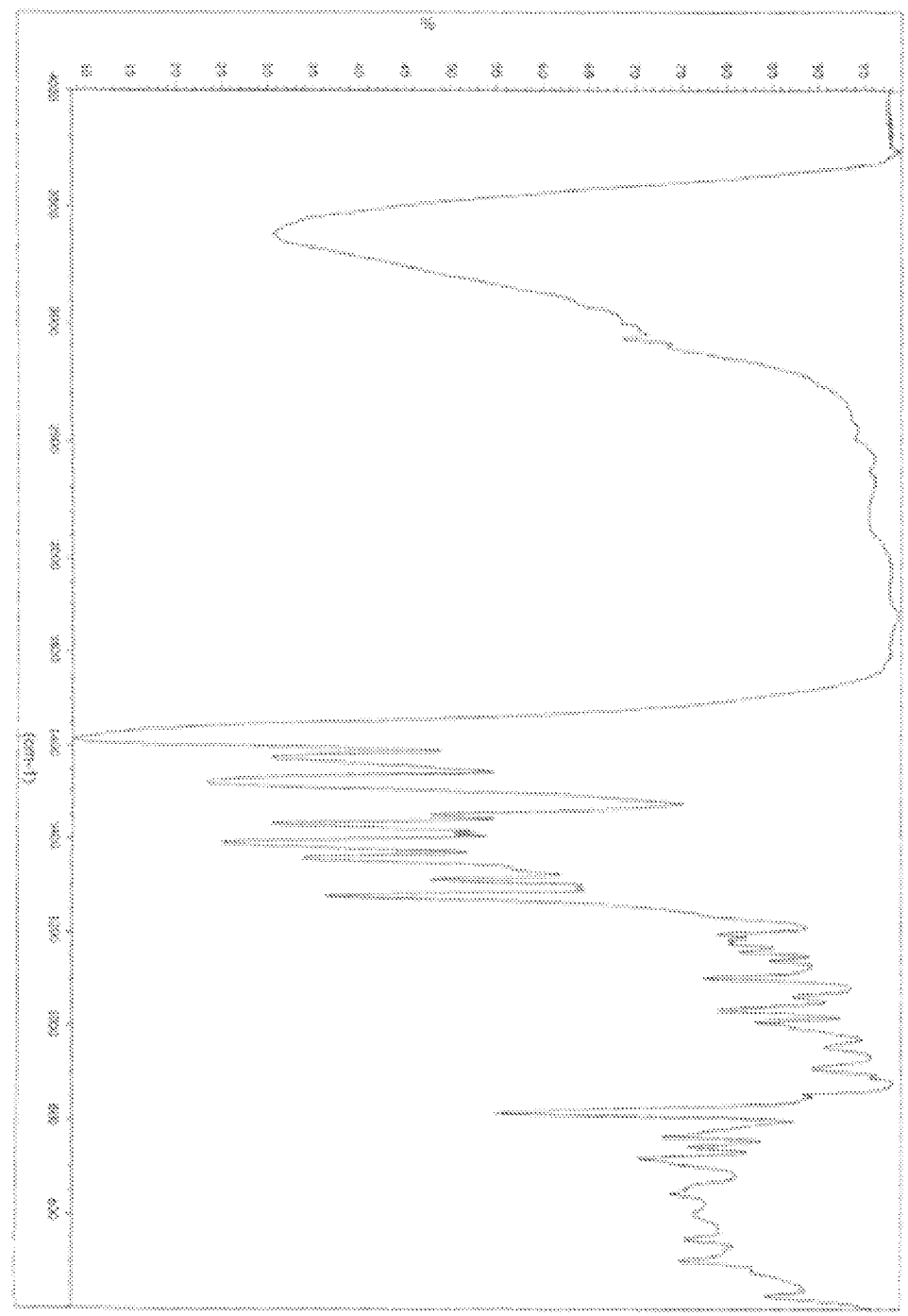
FIG. 15 shows an IR spectrum of the compound of Example 8.

According to an embodiment, the sodium salt has characteristic peaks in the IR spectrum at (cm$^{-1}$): 3370, 1630, 1580, 1520, 1430, 1390, 1360, 1280 and 630. In particular, the sodium salt is characterized by the IR spectrum as shown in FIG. 15.

Figure 16:
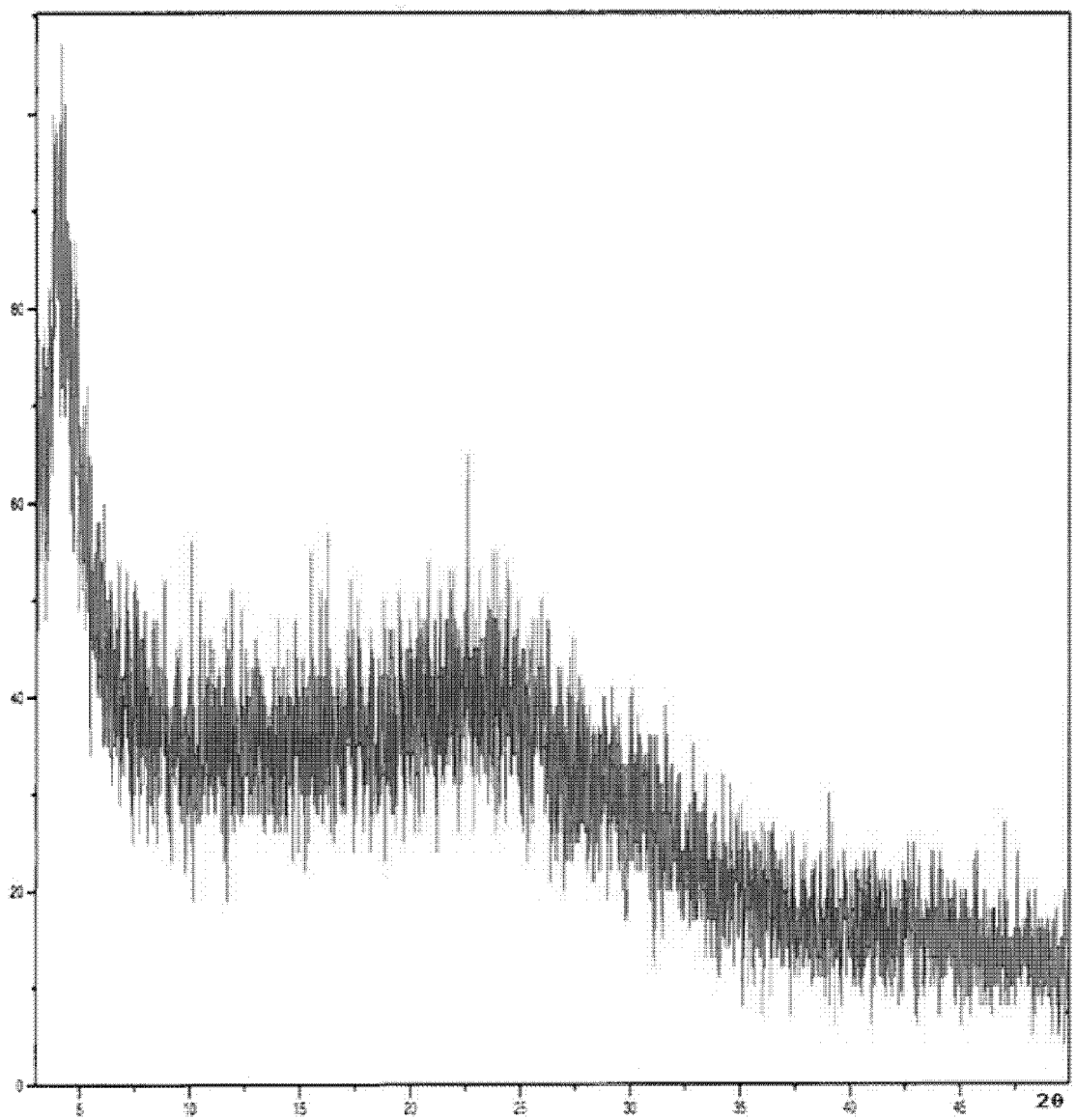
FIG. 16 shows a powder X-ray diffraction pattern of the compound of Example 8.

According to an embodiment, the sodium salt is characterized by the powder X-ray diffraction pattern as shown in FIG. 16.

The acid addition salts can be obtained by reaction of the des-fluoroquinolone free base (I) with the corresponding acid. In turn, the alkaline salts can be obtained by reaction of (I) with the corresponding hydroxide. A great variety of solvents can be used in the salification processes. Non-limitative examples of suitable solvents are ethyl acetate, ethanol, mixtures of ethanol and water, dimethyl sulfoxide, t-butyl methyl ether, acetonitrile, and the like, and mixtures thereof.

The compounds of the present invention can be formulated, together with appropriate excipients, carriers, and diluents in pharmaceutical compositions suitable for systemic administration. Such compositions include those wherein significant blood levels of drug are required, and they are useful in the treatment or prevention of some bacterial infections in humans and animals. The compounds of the present invention may be administered by oral or parenteral administration in the form of tablets, capsules, powder, syrup, granules, pills, suspensions, emulsions, liquids, powdery preparations, suppositories, eye drops, nasal drops, ear drops, dressings, ointments, or injections in accordance with conventional methods. The administration methods, doses and number of times of administration can be selected appropriately depending on the age, weight and symptom of patients. Usually, the compounds of the present invention may be administered to adults at a dose of 0.1 to 100 mg/kg at a time or in several times in portions by oral or parenteral administration (for example, injection, drip infusion and administration to rectal portion). Particular infections to be treated or prevented include those produced by all kinds of bacteria susceptible to the des-fluoroquinolone compound (I).

Throughout the description and claims the word "comprise" and variations of the word, such as "comprising", are not intended to exclude other technical features, additives, components, or steps. Additional objects, advantages and features of the invention will become apparent to those skilled in the art upon examination of the description or may be learned by practice of the invention. The following examples are provided by way of illustration, and are not intended to be limiting of the present invention.

EXAMPLES

Instruments

FT-Raman
Bruker RFS100.
  Nd:YAG 1064 nm excitation, 300 mW laser power, Ge detector, 64 scans, range 25-3500 cm$^{-1}$, 2 cm$^{-1}$, resolution.
IR
Thermo Nicolet Nexus.
  15798 cm$^{-1}$ laser frequency, DTGS KBr detector, 32 scans, range 400-4000 cm$^{-1}$, 4 cm$^{-1}$ resolution.
Powder X-Ray Diffraction Pattern (FIGS. 8, 10, 12, and 14)
  X-ray diffractometer Bruker D8 Advance with CuKα-radiation (Instrument Nr. G.16.SYS.S013); Standard measuring conditions: tube power 35 kV/45 mA, step size 0.017° (2Theta), step time 105±5 sec, scanning range 2-50° (2Theta), the divergence slit is set to variable V12; the samples were rotated; detector Vantec1, opening angle 3°, # of channels 360±10.
  Sample holders: Silicon single crystal.
  Sample dimensions, depth/diameter: 1.0 mm/12 mm or 0.5 mm/12 mm or 0.1 mm/≈12 mm.
  The y-axis (counts or CPS) of the diffractogram does not show the total intensity (/sec) but the value intensity/# active detector channels (/sec).
Powder X-Ray Diffraction Pattern (FIG. 16)
  X-ray diffractometer PANalytical X'Pert PRO MPD with CuKa-radiation; Standard measuring conditions: tub power 45 kV/40 mA, step size 0.017° (2Theta), step time 300 sec, scanning range 2-50° (2 Theta), Slit 0.19 mm, detector X'Celerator.

Example 1

1-Cyclopropyl-8-methyl-7-[5-methyl-6-(methylamino)-3-pyridinyl]-4-oxo-1,4-dihydro-3-quinolinecarboxylic acid citrate salt ($C_{21}H_{21}N_3O_3 \cdot C_6H_8H_7$)

A mixture of the desfluoroquinolone compound (I) (100.3 mg) and citric acid (52.7 mg) was treated in a ball mill (90 min, 30 Hz) with an addition of ethyl acetate (50 μL). The obtained powder was shaken in ethyl acetate (0.5 mL) with a temperature cycle (T1=25° C., T2=30° C., 500 rpm). After overnight, the suspension was filtered and the solid was dried in vacuum.

The FT-spectrum is shown in FIG. 1.
The powder X-ray diffraction pattern is shown in FIG. 2. The axis of the ordinates shows the diffraction intensity expressed in Lin(cps).

Example 2

1-Cyclopropyl-8-methyl-7-[5-methyl-6-(methylamino)-3-pyridinyl]-4-oxo-1,4-dihydro-3-quinolinecarboxylic acid hemi-fumarate salt ($C_{21}H_{21}N_3O_3 \cdot 0.5C_4H_4O_4$)

A mixture of (I) (100 mg) and fumaric acid (35 mg) was treated in a ball mill (90 min, 30 Hz) with an addition of ethyl acetate (50 μL). The obtained solid was shaken in ethanol (1 mL) with a temperature cycle (T1=25° C., T2=30° C., 600 rpm). After overnight, the suspension was filtered and the solid was dried in vacuum.

The FT-spectrum is shown in FIG. 3.
The powder X-ray diffraction pattern is shown in FIG. 4. The axis of the ordinates shows the diffraction intensity expressed in counts/s.

Example 3

1-Cyclopropyl-8-methyl-7-[5-methyl-6-(methylamino)-3-pyridinyl]-4-oxo-1,4-dihydro-3-quinolinecarboxylic acid maleate salt ($C_{21}H_{21}N_3O_3 \cdot C_4H_4O_4$)

A mixture of (I) (99.8 mg) and maleic acid (31.9 mg) was treated in a ball mill (90 min, 30 Hz) with an addition of ethanol:water (1:1) (50 μL). The obtained solid was shaken in ethanol (1 mL) with temperature cycle (T1=25° C., T2=30° C., 500 rpm). After overnight, the suspension was filtered and the solid was dried in vacuum.

The FT-spectrum is shown in FIG. 5.

The powder X-ray diffraction pattern is shown in FIG. 6. The axis of the ordinates shows the diffraction intensity expressed in Lin(cps).

Example 4

1-Cyclopropyl-8-methyl-7-[5-methyl-6-(methylamino)-3-pyridinyl]-4-oxo-1,4-dihydro-3-quinolinecarboxylic acid L-tartrate salt
($C_{21}H_{21}N_3O_3 \cdot C_4H_6O_6$)

A mixture of (I) (100.1 mg) and L-tartaric acid (41.2 mg) was treated in a ball mill (90 min, 30 Hz) with an addition of ethyl acetate (50 µL). The obtained solid was shaken in ethyl acetate (1 mL) with a temperature cycle (T1=25° C., T2=30° C., 500 rpm). After overnight, the suspension was filtered and the solid was dried in vacuum.

The FT-spectrum is shown in FIG. 7.

The powder X-ray diffraction pattern is shown in FIG. 8. The axis of the ordinates shows the diffraction intensity expressed in Lin(cps).

Example 5

1-Cyclopropyl-8-methyl-7-[5-methyl-6-(methylamino)-3-pyridinyl]-4-oxo-1,4-dihydro-3-quinolinecarboxylic acid mesylate salt
($C_{21}H_{21}N_3O_3 \cdot CH_4O_3S$)

The compound (I) (100 mg) and methanesulfonic acid (17.9 µL) were dissolved in dimethyl sulfoxide (10 mL). The clear solution was evaporated and the obtained solid was shaken in t-butyl methyl ether (2 mL) with a temperature cycle (T1=25° C., T2=30° C., 500 rpm). After overnight, the suspension was filtered and the solid was dried in vacuum.

The FT-spectrum is shown in FIG. 9.

The powder X-ray diffraction pattern is shown in FIG. 10. The axis of the ordinates shows the diffraction intensity expressed in Lin(cps).

Example 6

1-Cyclopropyl-8-methyl-7-[5-methyl-6-(methylamino)-3-pyridinyl]-4-oxo-1,4-dihydro-3-quinolinecarboxylic acid hydrochloride monohydrate salt
($C_{21}H_{21}N_3O_3 \cdot HCl \cdot H_2O$)

The compound (I) (200.4 mg) was dissolved in HCl (0.1N) (5.5 mL) and additional $H_2O$ (60 mL) and ethanol (10 mL). The suspension was stirred for two hours and filtered. The clear solution was evaporated ($N_2$) and the obtained yellow solid was dried in vacuum and then shaken in t-butyl methyl ether (4 mL) with a temperature cycle (T1=25° C., T2=30° C., 500 rpm). After one day the suspension was filtered and the solid was dried in vacuum. Acetonitrile (4 mL) was added to the solid and the suspension was treated in a ultrasonic bath (10 min) and than shaken (30 min) at 25° C. The suspension was filtered and dried in vacuum.

The FT-spectrum is shown in FIG. 11.

The powder X-ray diffraction pattern is shown in FIG. 12. The axis of the ordinates shows the diffraction intensity expressed in counts/s.

Example 7

1-Cyclopropyl-8-methyl-7-[5-methyl-6-(methylamino)-3-pyridinyl]-4-oxo-1,4-dihydro-3-quinolinecarboxylic acid potassium salt, $C_{21}H_{20}KN_3O_3$ The compound (I) (100 mg) was dissolved in $H_2O$ (5 mL) with addition of KOH (0.05M) (5.5 mL). The solution was filtered, evaporated and the amorphous residue was shaken in acetonitrile (0.5 mL) (temperature cycle: T1=25° C., T2=30° C., 600 rpm) resulting in the formation of a white solid. After one day additional acetonitrile (1 mL) was added and the suspension was shortly treated in a ultrasonic bath and then shaken with the same temperature cycle like before. After two hours the suspension was filtered and the solid was dried in vacuum.

The FT-spectrum is shown in FIG. 13.

The powder X-ray diffraction pattern is shown in FIG. 14. The axis of the ordinates shows the diffraction intensity expressed in Lin(cps).

Example 8

1-Cyclopropyl-8-methyl-7-[5-methyl-6-(methylamino)-3-pyridinyl]-4-oxo-1,4-dihydro-3-quinolinecarboxylic acid sodium salt, $C_{21}H_{20}N_3NaO_3$ The compound (I) (22.87 g) was suspended in $H_2O$ (130 mL). An aqueous solution of NaOH (0.5M) (126 mL) was added for 1 h 20 min. Then an aqueous solution of NaOH (1%) (1.3 mL) was added. After shaking the mixture for 1 h, the pH stabilized at 10.99-11.00, and the mixture showed cloudiness. Then 25 mL of water was added and shaken for 15 min. Another portion of water (25 mL) was added and the mixture was shaken for 15 min more. The solution was cooled and a solid was obtained and lyophilized.

The IR spectrum is shown in FIG. 15.

The powder X-ray diffraction pattern is shown in FIG. 16. The axis of the ordinates shows the diffraction intensity expressed in Lin(cps).

Example 9

Aqueous Solubility

To determine the aqueous solubility of the salts, suspensions of the salts were shaken 2 h at 20° C. and 400 rpm. Amounts of the salts and the corresponding volumes of water are summarized in Table 1. Afterwards the mixtures were filtered (0.1 µm centrifuge filter) and the concentrations were determined by HPLC.

TABLE 1

| Salt | Weight of salt (mg) | Volume of water (mL) |
| --- | --- | --- |
| Free drug | 12 | 0.5 |
| Citrate | 19 | 0.5 |
| Hemi-fumarate | 5 | 0.25 |
| Maleate | 13 | 0.5 |
| L-Tartrate | 12 | 0.5 |
| Mesylate | 10-15 | 0.1 |
| Hydrochloride monohydrate | 40 | 0.2 |
| Potassium | 10-15 | 0.1 |
| Sodium | 85 | 0.4 |

The solubility of the salts in water determined by HPLC is shown in Table 2.

TABLE 2

| Salt | HPLC area | Dilution factor | Injected volume μL | Solubility in H$_2$O mg/mL | pH |
| --- | --- | --- | --- | --- | --- |
| Free drug | 719897 | 5 | 10 | 0.0190 | 8.5 |
| Citrate | 6030413 | 100 | 10 | 5.2155 | 2.7 |
| Hemi-fumarate | 2898884 | 5 | 10 | 0.0897 | 4.8 |
| Maleate | 3931283 | 5 | 10 | 0.1489 | 5.3 |
| L-Tartrate | 6057774 | 100 | 10 | 4.5986 | 2.5 |
| Mesylate | 3415772 | 5000 | 10 | 113.4631 | 2.4 |
| Hydrochloride monohydrate | 649381 | 500 | 10 | 2.0 | 2.8 |
| Potassium | 3334195 | 5000 | 10 | 109.0430 | 9.8 |
| Sodium | 1333377 | 100 | 10 | 159 | 9.0 |

The invention claimed is:

1. A pharmaceutical salt of 1-cyclopropyl-8-methyl-7-[5-methyl-6-(methylamino)-3-pyridinyl]-4-oxo-1,4-dihydro-3-quinolinecarboxylic acid hydrochloride monohydrate having a solubility of $\geq 0.050$ mg/mL of water and having characteristic peaks in the powder X-ray diffraction pattern at (2θ): 9.5, 25.4 and 26.0; or at 8.6, 9.5, 14.7, 16.7, 20.6, 25.4, 26.0 and 29.8.

2. A pharmaceutical composition comprising a pharmaceutical salt of claim 1 as an active ingredient.

3. A pharmaceutical salt of claim 1 for use as a medicament.

4. A pharmaceutical salt of claim 1 for use in the treatment or prevention of bacterial infections.

5. Method of treating a subject suffering or being at risk of a bacterial infection by administering a therapeutically effective amount of a pharmaceutical salt of claim 1.

* * * * *